United States Patent [19]

Buckland

[11] Patent Number: 4,876,182

[45] Date of Patent: Oct. 24, 1989

[54] PHOTOGRAPHIC ELEMENTS CONTAINING PYRAZOLONE COLOR COUPLERS

[75] Inventor: Paul R. Buckland, Marshalswick, Great Britain

[73] Assignee: Eastman Kodak COmpany, Rochester, N.Y.

[21] Appl. No.: 358,098

[22] Filed: May 30, 1989

[30] Foreign Application Priority Data

Jun. 21, 1988 [GB] United Kingdom ............... 8814676

[51] Int. Cl.$^4$ ............................................. G03C 7/38
[52] U.S. Cl. ..................................... 430/555; 430/544; 430/957
[58] Field of Search ............... 430/554, 555, 544, 957

[56] References Cited

U.S. PATENT DOCUMENTS

| | | | |
|---|---|---|---|
| 3,227,554 | 1/1966 | Barr et al. | 430/553 |
| 4,351,897 | 9/1982 | Aoki et al. | 430/555 |
| 4,556,630 | 12/1985 | Furutachi et al. | 430/555 |
| 4,584,266 | 4/1986 | Hirose et al. | 430/555 |

OTHER PUBLICATIONS

*Chem. Abstracts* 102:36593j; "Color Photographic Image Formation", 1985, Abst. of Japanese 59/57,240.

*Primary Examiner*—Richard L. Schilling
*Attorney, Agent, or Firm*—Thomas F. Kirchoff

[57] ABSTRACT

A photographic element is described which contains a pyrazolone color coupler compound which provides a dye having improved fastness to light and improved resistance to yellowing when compared with prior known coupler compounds.

5 Claims, No Drawings

PHOTOGRAPHIC ELEMENTS CONTAINING PYRAZOLONE COLOR COUPLERS

This invention relates to photographic elements containing pyrazolone color couplers.

It is well established in the photographic art that color images may be obtained from imagewise exposed silver halide emulsions by developing them with a primary aromatic amine color developing agent in the presence of a color coupler. The oxidized color developing agent formed in the areas of silver halide development couples with the coupler to form a dye. The coupler may be present in the developer solution but is normally incorporated in the sensitive photographic material.

It is known that pyrazolones having a coupling-off group in the 4-position behave as 2-equivalent couplers producing approximately one mole of dye for every two equivalents of silver produced during color development. Among the coupling-off groups known in this connection are the arylthio groups as described, for example, in U.S. Pat. Nos. 3,227,554, 4,351,897, 4,556,630 and 4,584,266.

Japanese specification 59/57240 (published Apr. 2, 1984) discloses a class of arylthiopyrazolone couplers in which the released arylthio coupling-off group undergoes an intramolecular nucleophilic substitution reaction so as to block the sulphur atom; preventing it from having any photographic effect. The specification discloses a coupler of the formula:

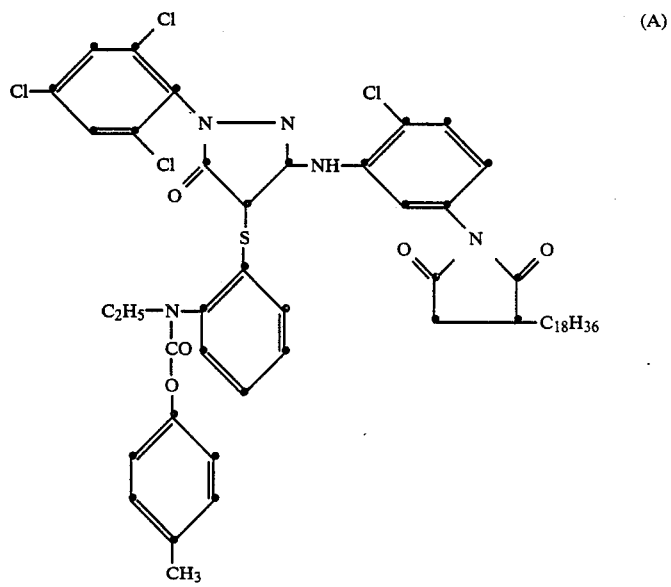
(A)

A problem with this class of coupler is that the image dye formed in the processed photographic coatings has rather low fastness to light.

A coupler which is commercially used and which is disclosed in U.S. Pat. No. 3,935,015 has the formula:

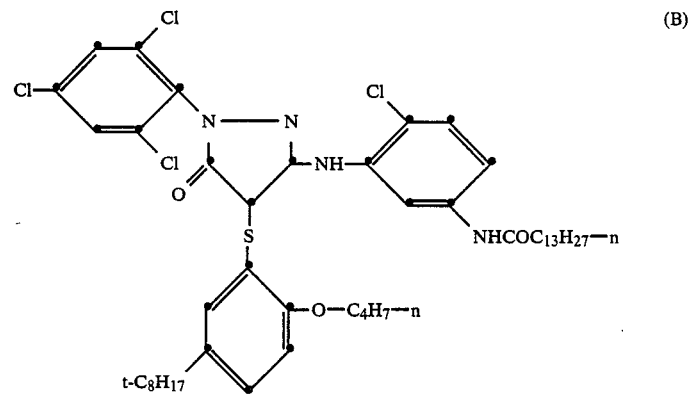
(B)

Coupler B forms undesirable stain in the processed photographic material and does not form the desired image dye density upon rapid machine processing. Also Coupler B does not achieve full dye density especially when machine processed without the presence of a Lippman fine grain silver halide emulsion being present in the photographic material and this is clearly undesirable.

Another commercially used coupler, which is described in U.S. Pat. No. 3,935,015, is Coupler C having the formula:

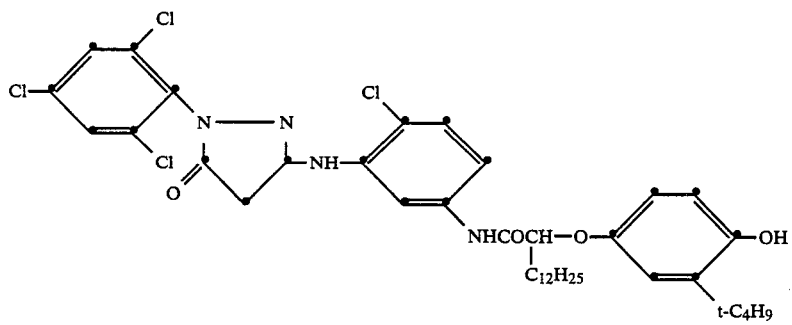

(C)

Coupler C forms dyes having undesirable low light fastness properties and causes yellowing in the processed photographic material on storage both in the light and in the dark.

The present invention provides couplers which form dyes having improved fastness to light and have improved resistance to yellowing compared to coupler (C).

Accordingly there is a provided a pyrazolone color coupler of the general formula:

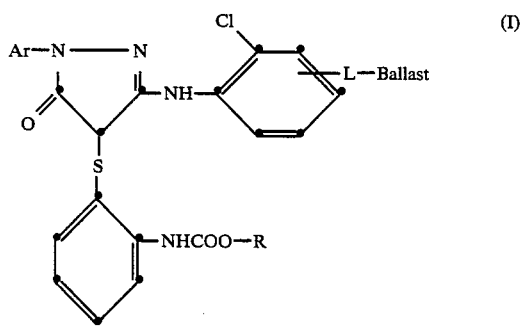

(I)

wherein:

Ar is a substituted or unsubstituted aryl group;

R is a substituted or unsubstituted alkyl or aryl group;

L is a direct bond or a linking group; and

Ballast is a group of such size and configuration as to render the coupler non-diffusible in photographic coatings.

In one form of the invention the group R has the general formula:

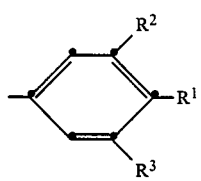

(II)

wherein:

$R^2$, $R^2$ and $R^3$ are each individually hydrogen, alkyl, alkoxy, aryloxy, acylamino or tertiary amino groups.

Alkyl groups which may be represented by R comprise from 1 to about 20 carbon atoms, such as butyl, pentyl, or dodecyl, or substituted alkyl groups, for example, benzyl.

Examples of Ar in Formula (I) are monochlorophenyl, 2,6-di-chlorophenyl, 2,4,6-tri-chlorophenyl, tetrachlorophenyl or penta-chlorophenyl groups.

Examples of groups $R^1$, $R^2$ and $R^3$ in Formula (II) are methyl, ethyl, propyl, n-butyl, t-butyl, n-decyl and n-dodecyl.

Examples of linking groups L are —NH—, —NHCO—, COHN—, —NHSO—, and —SI$_2$NH—.

Examples of Ballast groups in Formula (I) include —C$_{13}$H$_{27}$—n and —C$_{15}$H$_{31}$—n.

The present invention provides a photographic element comprising a support and a photosensitive silver halide emulsion layer which has associated therewith a dye-forming coupler (I) above.

The present couplers may be prepared from the corresponding 4-equivalent pyrazolone coupler by reaction with a sulphenyl bromide of the formula:

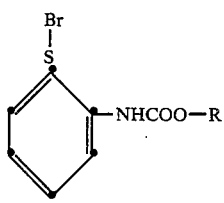

for example in dimethylformamide with or without triethylamine as catalyst.

Specific examples of couplers according to the present invention are set out below in Table I.

TABLE I

[Structure: Ar-N-N pyrazolone with S-phenyl-NHCOO-R substituent and NH linkage to chloro-phenyl-NHCO-Ballast]

| Coupler Number | R | Ballast | Ar | Melting Point (°C.) |
|---|---|---|---|---|
| 1 | 4-($C_{12}H_{25}$-n)-phenyl | —$C_{15}H_{31}$—n | 2,4,6-trichlorophenyl | 107 |
| 2 | 4-(Bu—t)-phenyl | " | " | 115 |
| 3 | 4-$CH_3$-phenyl | " | " | 116 |
| 4 | 4-$OCH_3$-phenyl | " | " | 111 |
| 5 | 2,4-di-(Bu—t)-phenyl | " | " | 128 |
| 6 | —$CH_2$-phenyl | —$C_{13}H_{27}$—n | " | 144 |
| 7 | 2,4-di-(Bu—t)-phenyl (t-Bu, Bu-t) | —$C_{15}H_{31}$—n | " | 123 |
| 8 | —$CH_2$-phenyl | —$C_{15}H_{31}$—n | " | 130 |
| 9 | 4-$CH_3$-phenyl | —$C_{13}H_{27}$—n | 2,3,4,5,6-pentachlorophenyl | 142 |

TABLE I-continued

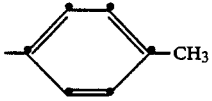

| Coupler Number | R | Ballast | Ar | Melting Point (°C.) |
|---|---|---|---|---|
| 10 | –C₆H₄–CH₃ | —C₁₅H₃₁—n | " | 145 |
| 11 | —CH₂—C₆H₅ | " | " | 163 |
| 12 | —CH₂CH₃ | " | " | 157 |
| 13 | —(CH₂)₁₁CH₃ | " | " | 151 |
| 14 | —(CH₂)₂NHSO₂—C₆H₄—CH₃ | " | " | 195 |
| 15 | —CH₂—CH(C₂H₅)—Bu—n | " | " | 148 |
| 16 | —CH₂—CH(C₂H₅)—O—C₆H₅ | " | " | 162 |
| 17 | —CH₂—C₆H₅ | —C₁₃H₂₇—n | " | 152 |
| 18 | —CH₂—C₆H₅ | —CH(Me)C₉H₁₉—n | " | 162 |
| 19 | —CH₂—C₆H₅ | —CH₂CH(Me)(CH₂)₃C(Me₂)OMe | " | 133 |
| 20 | —CH₂—C₆H₅ | —CH(C₁₂H₂₅-n)—O—C₆H₃(OH)(Bu-t) | " | glass |

The dye-forming couplers of this invention can be used in the ways and for the purposes that dye-forming couplers have been previously used in the photographic art.

Typically, the couplers are associated with a silver halide emulsion layer coated on a support to form a photographic element. As used herein, the term "associated therewith" signifies that the coupler is incorporated in the silver halide emulsion layer or in a layer adjacent thereto where, during processing, it is capable of reacting with silver halide development products.

The photographic elements can be single color elements or multicolor elements. In a multicolor element, the magenta dye-forming couplers of this invention would usually be associated with a green-sensitive emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively, at least one of the magenta dye-forming couplers being a coupler of this invention. The element can contain additional layers, such as filter and barrier layers.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The silver halide emulsion employed in the elements in this invention can be either negative-working or positive-working. suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII), paragraphs I and J), light absorbing and scattering materials (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section VIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methanesulphonamido)ethylaniline sulphate hydrate, 4-amino-3-methyl-N-ethyl-N-$\beta$hydroxyethylaniline sulphate, 4-amino3-$\beta$-(methanesulphonamido)ethyl-N,N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic development agent to development exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following Examples are given for a better understanding of the invention. All temperatures are in °C.

Synthesis: Preparation of Coupler (11)

DISULPHIDE PRECURSOR TO COUPLER (11)

95% Benzylchloroformate (42.6 g. 0.25 mole) was added in one portion to a stirred mixture of o-aminophenyl disulphide (25 g, 0.1 mole), sodium bicarbonate (25.2 g, 0.3 mole) and tetrahydrofuran (100 ml) at 5°. The cooling bath was removed, whereupon the temperature rose to 27° C. over 10 minutes. After stirring for a further ½ hour at room temperature, the mixture was heated to 45° and stirred at this temperature for a further 9 hours. The mixture was filtered to remove inorganic salts and the solvent removed by distillation. Hot ligroin (500 ml) was added to the yellow oil and on cooling a white solid was obtained, which was collected, washed with petroleum ether (bp 60°-80° C.) and dried to give the product (45.0 g, 87%), m.p. 97°, one spot t.l.c. (4:1 petroleum ether:EtOAc).

COUPLER (11)

Bromine (4.9 g, 0.031 mole) was added to ice cold dimethylformamide (5 ml) and the mixture added with stirring to a solution of the disulphide (15.82 g, 0.031 mole) in dimethylformamide (175 ml) at room temperature. Coupler (F) (see below) (42.52 g, 0.06 mole) was added and stirring continued until dissolution of the solid was complete (5 minutes). The solution was cooled to 5° and triethylamine (18.6 g, 0.18 mole) added, which caused the temperature to rise to 20°. After stirring for a further ½ hour at room temperature, the mixture was quenched with 1M hydrochloric acid (2000 ml), to yield a solid which was dissolved in ethyl acetate (500 ml). The solution was washed successively with 1M hydrochloric acid (3×500 ml) and saturated salt (NaCl) solution (500 ml). The solution was dried and ethyl acetate (350 ml) removed to give on cooling and stirring (overnight) a white solid. This was collected centrifugally and the solid washed with ice cold ethyl acetate (4×100 ml), applying centrifugal force after each washing. The resulting material was vacuum dried at 50° to yield the product 42.7g, 74%) as a white solid m.p. 163°. Found: C,55.4; H, 5.0; Cl,21.6; N,7.1; Sm3.3. $C_{45}H_{49}Cl_6N_5O_4S$ requires C,55.8; H,5.1; Cl,22.0; N,7.2; S,3.3% HPLC 97%, N.M.R. and mass spectra consistent with proposed structure.

Coupler (F) has the formula:

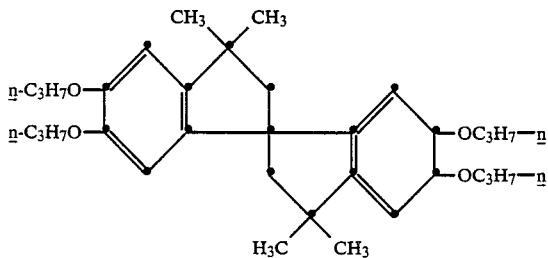

Other couplers of this invention, e.g. Coupler (1), can be made using a similar method.

Photographic Example I:

The following compounds were used in the coupler dispersions described below.

(Compound No. 21 in U.S. Pat. No. 4,360,589)  A-1

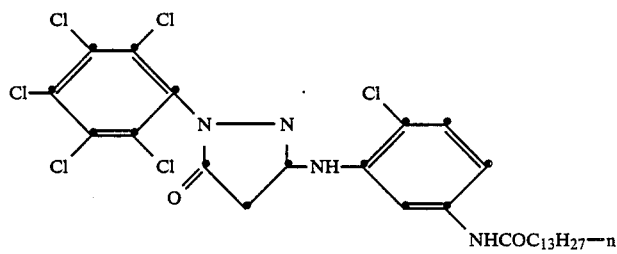

(Compound No. II-10 in EP 81,768)  A-2

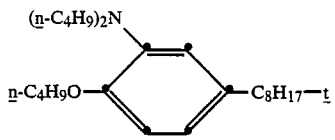

Tricresyl phosphate  A-3

(Compound No. I-1 in U.S. Pat. No. 4,217,410)  A-4

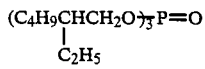

(Compound No. 104 in EP 69,070)  A-5

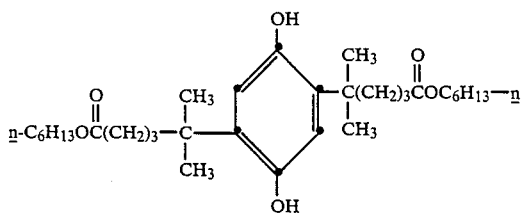

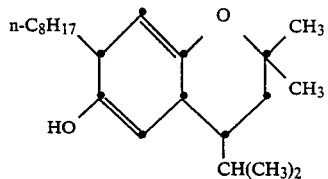

A-6

A coupler dispersion was prepared so as to contain coupler (31%), A1 (9%), A2 (10%), A3 (30%), A4 (15%), A5 (5%) and ethyl acetate [(3×weight of coupler used) ml]. This was coated together with gelatin, a silver chloride emulsion and a mixture of surfactants (Alkanol$^R$ XC (Olin Corporation) 10g) on a gel-subbed, polyethylene-coated paper support, to give a photosensitive layer containing coupler at 0.380 mmol/m², silver chloride at 172mg(Ag).M² and gelatin at 1240mg/m². On top of this layer is coated a mixture of hardener (bisvinylsulphonylmethyl ether) in gelatin to give an overcoat layer containing gelatin at 1080mg/m² and hardener at 2% by weight based on total gelatin.

Samples of each element were imagewise exposed through a graduated step tablet, then processed at 35° C. (45 sec. in a color developer, 45 sec. in a bleach-fix bath), washed and dried. The color developer used is disclosed in E. P. Application No. 8700926.4 Published Mar. 24, 1988. The bleach-fix bath (pH 6.8) consisted of:

| | |
|---|---|
| Ammonium thiosulphate | 104.0 g |
| Sodium hydrogen sulphite | 13.0 g |
| Ferric ammonium ethylene diamine tetraacetic acid | 65.6 g |
| EDTA | 6.56 g |
| Ammonium hydroxide (28%) | 27.9 ml |
| Water to make | 1 L |

Dye images of replicate processed strips were then subjected to stability and yellowing tests at 60° C., 70% RH and 77° C., 15% RH with the following results (all results×100).

| Coupler No. | 2 weeks 50klux daylight from 1.7 | 1.0 | 4 Weeks 60C, 70RH yellowing | 4 Weeks 77C 15RH yellowing |
|---|---|---|---|---|
| 1 | −20 | −22 | 1 | 6 |
| 7 | −26 | −21 | 2 | 12 |
| 8 | −18 | −14 | 2 | 12 |
| C* | −35 | −30 | 14 | 16 |

*Coupler (C) dispersion comprised coupler (C) (49%), di-n-butyl phthalate (24.5%), A6 (21.5%) and dioctyl-hydroquinone (5%).

In the above table comparative coupler (C) has formula (C) above.

As can be seen couplers 1, 7 and 8 have superior resistance to yellowing and form dyes of superior lightfastness compared to prior art coupler (C).

Photographic Example 2

The procedure of Example I is repeated to compare Coupler 3 of the invention with prior art couplers B, C and A'. Coupler A' is closely similar to prior art Coupler A above and is expected to behave similarly. The results are as follows (all results×100).

| Coupler | 2 weeks 50 klux daylight from: | | |
|---|---|---|---|
|  | 1.7 | 1.0 | 0.5 |
| 3 | −24 | −16 | −11 |
| B | −27 | −20 | −15 |
| A' | −58 | −30 | −13 |
| C* | −32 | −26 | −18 |

*formulation as in Example I.

The dye formed from Coupler 3 has superior lightfastness compared to that from prior art couplers B, A' and C.

Coupler A' has the formula:

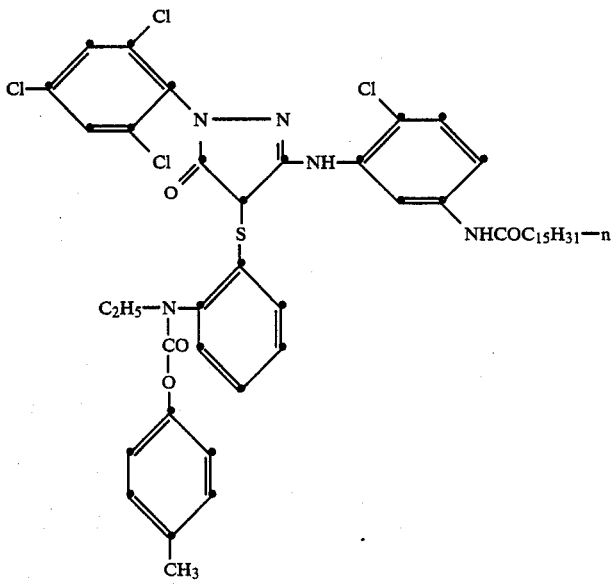

I claim:

1. A photographic element comprising a support and a photosensitive silver halide emulsion layer which has associated therewith a dye-forming coupler compound having the structural formula:

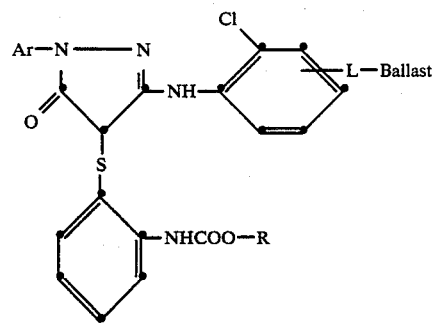

wherein:
Ar is a substituted or unsubstituted aryl group;
R is a substituted or unsubstituted alkyl or aryl group;
L is a direct or a linking group; and
Ballast is a group of such size and configuration as to render the coupler non-diffusible in photographic coatings.

2. The element of claim 1 wherein R has the formula:

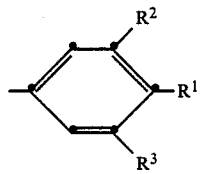

wherein:
$R^1$, $R^2$ and $R^3$ are each individually hydrogen, alkyl, alkoxy, aryloxy, acylamino or tertiary amino groups.

3. The element of claim 1 wherein R is a butyl, pentyl, dodecyl or benzyl group.

4. The element of claim 1 wherein Ar is a monochlorophenyl, 2,6-dichlorophenyl, 2,4,6-trichlorophenyl, tetrachlorophenyl or pentachlorophenyl group.

5. The element of claim 1 wherein L is an —NH—, —NHCO—, —CONH—, —NHSO₂— or —SO₂NH group.

* * * * *